United States Patent [19]

Eingorn

[11] Patent Number: 4,667,660

[45] Date of Patent: May 26, 1987

[54] UNIVERSAL ORTHOPEDIC TRACTION TONGS ASSEMBLY

[75] Inventor: David S. Eingorn, Yardley, Pa.

[73] Assignee: Ace Medical Company, Los Angeles, Calif.

[21] Appl. No.: 702,897

[22] Filed: Feb. 19, 1985

[51] Int. Cl.[4] .......................... A61H 1/02; A61B 17/36

[52] U.S. Cl. .......................... 128/75; 128/303 B

[58] Field of Search .......................... 128/346, 303 B, 75, 128/76 R

[56] References Cited

U.S. PATENT DOCUMENTS

| | | | |
|---|---|---|---|
| 3,604,412 | 9/1971 | Gardner | 128/75 |
| 3,923,046 | 12/1975 | Heifetz | 128/75 |
| 4,169,478 | 10/1979 | Hickmann | 128/346 |
| 4,360,028 | 11/1982 | Barbier et al. | 128/303 B |
| 4,444,179 | 4/1984 | Trippi | 128/75 |

*Primary Examiner*—Richard J. Apley
*Assistant Examiner*—H. Macey
*Attorney, Agent, or Firm*—Grant L. Hubbard

[57] ABSTRACT

A cervical traction tong assembly for mounting cranial pins to the head of a spinal fracture patient. The cervical tong assembly includes an arcuate central support member having a pair of movable coupling assemblies connected to the ends thereof for radial movement relative to the central support. A pair of straps for carrying cranial pins are rotatably mounted to each of the coupling assemblies. The coupling assemblies and the rotatable straps may be adjusted to position cranial pins at desired locations upon a patient's head and to provide a traction force vector at any predetermmed angle.

6 Claims, 4 Drawing Figures

Fig. 1
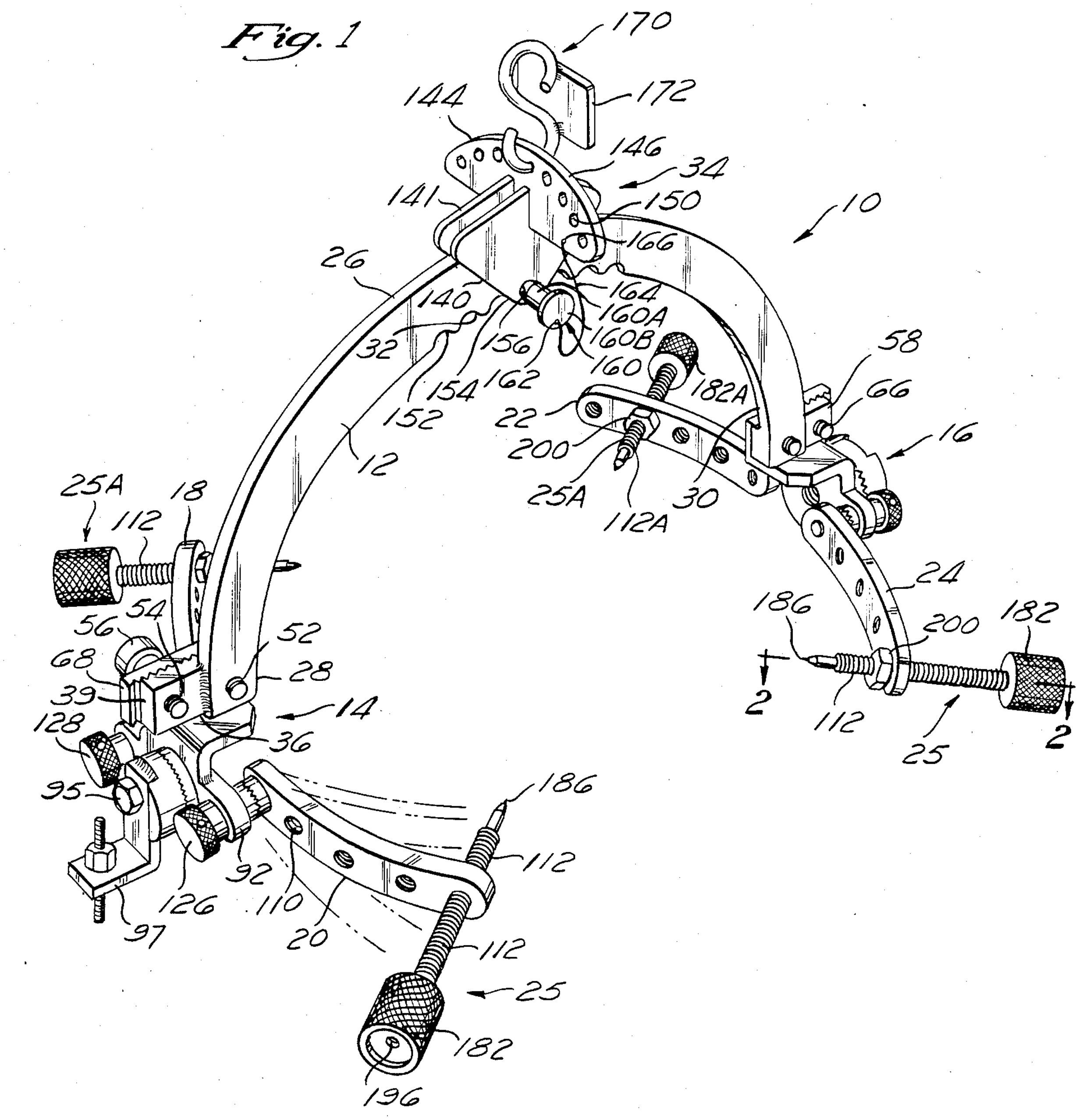
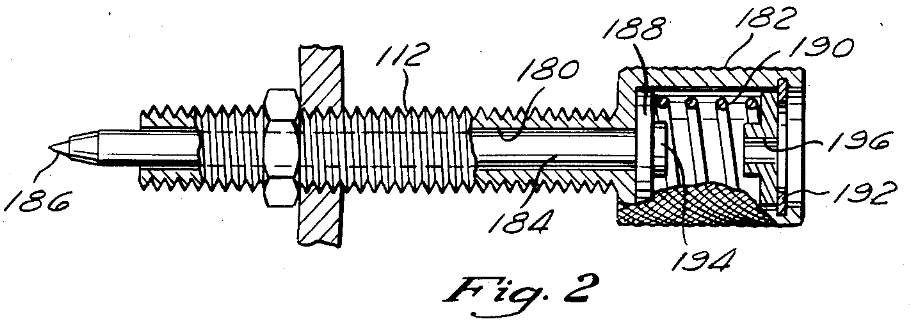
Fig. 2

UNIVERSAL ORTHOPEDIC TRACTION TONGS ASSEMBLY

BACKGROUND OF THE INVENTION

This invention relates generally to external fixation devices and particularly to external fixation devices for restraining the head of a person having a neck or back injury. Still more particularly, this invention relates to external fixation devices for attachment to a person's skull by pins that penetrate into small holes drilled into the person's skull.

Cervical skeleton traction is used to treat the unstable spine, to treat signal fractures and to accomplish reduction of cervical facet dislocations. In the past, skeleton traction has been applied utilizing caliper-like devices and halo-type rings. Both types of devices use pins which are drilled or screwed through the scalp into the skull to allow force vectors to be applied to the skull and spinal structure.

Exemplary of the caliper devices of the prior art are the Crutchfield Tongs. This device has two arms fastened together in the shape of an "X" and is pivotable at the intersection of the two arms. At the scalp end of each arm, a pin is affixed for penetration into pre-drilled skull holes. At the other end of each arm, there is a threaded rod and thumb screw structure which, when operated, tends to force the pin ends of the tong arms together or apart in accordance with the direction in which the thumb screw was turned. These tongs are applied to the top of the head with one pin on each side of the longitudinal axis of the spine. The pins are roughly perpendicular to the scalp, but because the tongs do not reach down around the head to a point just above the ears, the angle of the scalp pins to the longitudinal axis of the spine is acute when viewed from the front or rear of the head. Accordingly, when tension is placed upon the Crutchfield Tongs, the angle of the pins is such that, if not tightly compressed by the thumb screw, it is possible to pull the Crutchfield Tongs completely out of the skull.

Only two pins are used in the Crutchfield Tongs. As a result, a pivot line was established between the contact points of the pivot points and the skull. Thus, flexion and extension of the skull in relation to the spine, i.e., tilting of thehead forward and rearward, was not possible with the Crutchfield Tongs. Further, traction using the Crutchfield Tongs confined the patient to bed such that ambulation was not possible.

Another example of caliper devices are Barton's tongs. The structure of Barton's tongs is similar to that of the Crutchfield device; however, the arms are longer such that the pins reach further down on the head toward the ear. The shape and length of the tong arms are such that the drills of Barton's tongs entered the skull horizontally at a point somewhere between the top of the head and the ear such that a 90° angle is formed with the longitudinal axis of the spine. Barton's tongs have a greater resistance to pulling out of the skull than Crutchfield's tong, because of the increased angles of the pins with respect to the spine.

Another example of this type of device is the Gardner tongs, which have a different structure than the Crutchfield tongs and are less likely to loosen under prolonged traction load than are Crutchfield's tongs. Gardner's tongs include a semicircular frame structure in the approximate shape of a horseshoe with threaded pin holes on each end of the horseshoe arms. The horseshoe is placed down over the patient's head such that the pins contact the skull at a point just above the ears and in line with the longitudinal axis of the spine. Thus, the plane defined by the two pins and the point of contact of the tongs with the traction line passes through the center line of the spine. Excessive anterior placement of the tongs resulted in a forward tilt of the head resulting in misalignment of the spine. Since only two pins are used, a pivot line is formed and it is not possible to apply flexion and extension force vectors in the anterior-posterior plane with this device.

Anterior-posterior positioning of pins is disclosed in Russian Pat. No. 633,526. That patent discloses a tong-like device with facility for affixing two pins on either side of the head. This patent also discloses a plurality of holes centered at the top of the horseshoe and spaced above its center line. This feature plus the four points of contact with the skull allows the skull to be canted from left to right by placing the hook of a traction line to the left or right of the centerline of the horseshoe.

The inconvenience and attendant additional risk of confining a patient to bed during extended traction resulted in the development of the halo-type device. The halo-type device consists of a circular frame with an upturned portion in the rear with the frame completely encircling the skull. Several pins are normally used to engage the skull, resulting in increased ability to control the force vectors of the traction force. Force is applied to the halo ring by means of two hooks which attach to the halo ring on either side of the head in line with the longitudinal axis of the spine. These hooks may be moved forward or rearward to control flexion and extension torques on the skull in the anterior-posterior plane. Further, the halo may be attached to a plaster body cast or a vest type structure with a supporting linkage to allow traction to continue while the patient ambulated. This mobility was the principal advantage of the halo ring, although another advantage exists in that there is no movement between the skull and fixation pins, which reduces the chance of infection of the scalp in the areas surrounding the pins.

Because the halo completely encircles the head, it is necessary during application that an assistant gently lift the patient's head from the stretcher or support the head off the end of the table to provide sufficient space for the ring to be positioned around the patient's head.

Generally, the halo ring is placed just above the external ear. Pins are inserted through threaded holes spaced around the ring and diagonally opposite pins were tightened simultaneously using torque screwdrivers. The pins are then locked into place with set screws.

A disadvantage of the halo is that x-ray films of the pin location in the skull are difficult to obtain and give deceptive images, unless the x-ray was made of each pin at an angle tangential to the skull at the point of entry of the pin. The halo type ring also generally leaves pin hole scars over the eyebrows because the anterior placement of the pins is generally in the forehead region.

An improved orthopedic traction tong apparatus disclosed U.S. Pat. No. 4,444,179 to Trippi, comprises the combination of a generally arcuate main support member which extends from one side to the other side, over the top of the head of the patient user of the device. Means located generally in the central portion of the arcuate support member are provided to apply tension at any predetermined angle, as measured with respect to an imaginary axis line extending vertically upward through the center of the head of the user patient when the tongs are in use, the vector angle being in the side-to-side relationship to the head of the user patient. The tension applying means also includes means for connecting the tongs to a source of tension at any predetermined angle, measured, when in use, with reference to the imaginary axis line, front-to-back of the head of the user patient.

A pair of pin support means are secured at each end of the arcuately configured main support member for securing cranial pins to the orthopedic traction tongs. Each of the pin supports comprises a generally arcuate member extending from an end of the main support member and partially around the head of the user patient for permitting cranial pins to be inserted into the skull at radially spaced intervals around the head of the user patient. The relationship of the main support means is therefore fixed with respect to the head of the user.

The fixation rods are secured to respective ends of the main support and to fix the position of the traction tongs with respect to a vest or other external supporting means structure, thus enabling force to be applied through the rods to the main support means. Each rod connecting means comprises a pair of relatively rotatble clamp elements and means for securing the clamp elements to each other in a fixed relationship for applying force and tension to the head of the user patient at a preselected angle. The rod connecting means may be secured to the fixation rods at different positions on the respective side of the user's head, and apply tensile force through the tongs to the head at a preselected position.

The entire disclosure of U.S. Pat. No. 4,444,179 to Trippi is hereby expressly incorporated herein by reference.

Even with the improvements achieved by the Trippi device, there are still difficulties encountered in cervical traction applications. Such devices are sometimes difficult to accomodate to a certain head sizes; and, since the pin support means are fixed relative to the main support member, it is not always convenient to place the cranial pins in desired locations to avoid interference with x-rays and to secure the pins in intake portions of the patient's skull. Accordingly, there is a need in the art for an improved cervical traction apparatus which provides universal adjustment of the position of the pin support means relative to the main support so that a position may position the cranial pins carried by the cervical traction apparatus at optimum locations for treating the patient.

SUMMARY OF THE INVENTION

The present invention overcomes and alleviates the difficulties associated with previous orthopedic cervical traction tongs. The present invention includes an orthopedic traction tong assembly for attachment to the head of a patient by cranial pins, for example, the Wells pins, for applying tension to the patient's head at selected vector angles measured with reference to an axis extending vertically through the central of the patient's head and a second axis that orthogonally intersects the first axis and extends through the center of the patient's head from front to back. The present invention comprises a main support formed generally in the configuration of a rigid arc for extending from one side of the patient's head, over the top of the patient's head, to the other side and a pair of coupling assemblies connected to opposite ends of the main support. Each coupling assembly is movably mounted on the main support so that the coupling assemblies may be moved generally radially inwardly or outwardly in relation to the arc formed by the main support. The invention further includes a pair of pin support means connected to each of the coupling assemblies for mounting cranial pins for attachment to the patient's skull. The pin support means are rotatably mounted to the coupling assemblies for permitting attachment of the cranial pins carried to selected locations on the patient's skull.

The coupling assemblies are preferably attached to the main support by brackets that include a pair of bracket portions having teeth and grooves that intermesh. A bolt secures the teeth of the first and second bracket portions together to prevent any movement of the coupling assembly relative to the main support when the cervical traction assembly is in use upon a patient. The coupler assemblies each preferably include a coupler body having a pair of generally perpendicular legs. A first leg is mounted to the main support member and the second leg includes means for mounting the pin support means to the coupler body.

The pin support means are preferably rotatably mounted to the coupler bodies and are preferably lockable in predetermined positions so that the cervical tongs assembly is substantially rigid when in use with a patient.

The cervical tongs assembly of the present invention may be used with known traction equipment by applying a force to a clamp fastened near the central portion of the main support means or by fixation rods that are mounted to the coupling assemblies. The hanger is adjustable upon the main support means so that the tension applied to the main support may be directed at any selected angle. The fixation rods are rotatably mounted to the second legs of the coupler bodies so that fixation rods may be attached to a vest, for example, when the cervical tongs assembly is used upon an ambulatory patient or a patient confined to a wheel chair, or for attachment to a bed or other device for a patient that is confined to a particular position.

BRIEF DESCRIPTION OF THE DRAWINGS

FIG. 1 is a perspective of the the cervical tongs of the present invention;

FIG. 2 is a cross-sectional view of a pin used with the cervical tongs of FIG. 1;

DESCRIPTION OF THE PREFERRED EMBODIMENT

Figure 3:
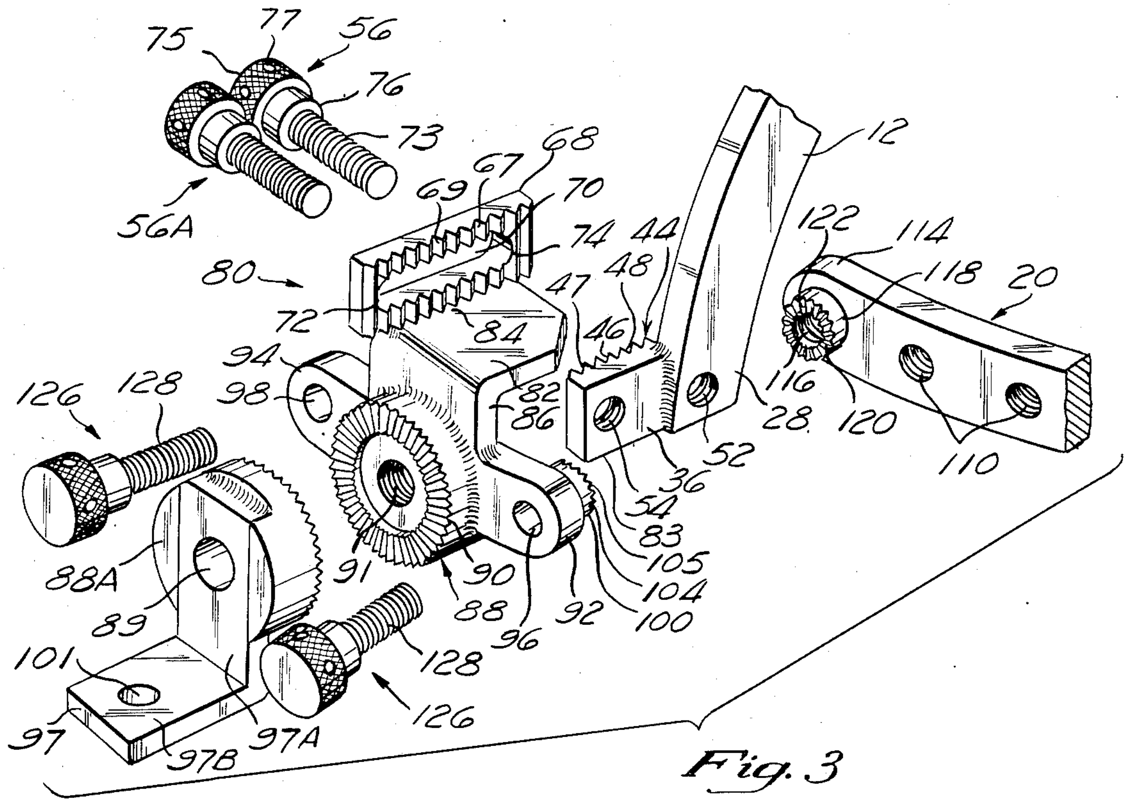
FIG. 3 is an exploded perspective view of a coupling assembly included in the cervical tongs of FIG. 1.

FIG. 1 shows the general configuration and components of a cervical tong assembly 10 according to the invention. The cervical tong assembly 10 includes a main support member 12, a pair of coupling assemblies 14 and 16, a pair of straps 18 and 20 pivotally connected to the coupling assembly 14, a pair of straps 22 and 24 pivotally connected to the coupling assembly 16, and a plurality of cranial pins 25 mounted to the straps 18, 20, 22 and 24.

As shown in FIGS. 1 and 2, the main support member 12 has a central portion 26 and a pair of opposing ends 28 and 30. The main support member 12 is preferably formed in a flat, rigid, curved configuration. The central portion 26 may be formed to have a generally U-shaped configuration or it may be formed as a continuous arc. As shown in FIG. 1, the central portion 26 may be approximately a semicircle. The central portion 26 preferably includes a plurality of notches 32 for mounting a hanger assembly 34 thereto.

Figure 4:
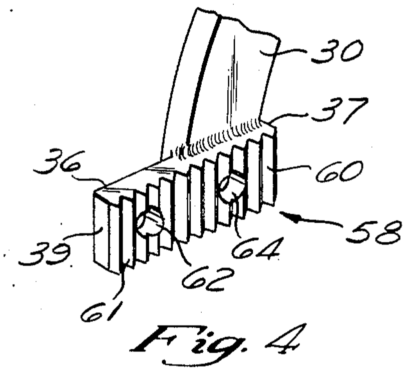
FIG. 4 is a perspective view of a portion of a bracket included in FIGS. 1 and 3.

As shown in FIGS. 1, 3 and 4, the end 28 includes a bracket portion 36 that may be formed generally as an elongate rectangle. The longer dimension of the rectangle is in approximate alignment with the radius of the arc formed by the support member 12. The bracket portion 36 has an inner end 37 that is generally flush with the inner portion of the arc of the main support member 12 at the end 28. The bracket portion 36 has an end 39 projects radially away from the arc formed by the main support member 12. The bracket portion 36 may be formed integrally with the end portion 28 by casting or forging, or it may be welded to the central portion 28. A surface 44 of the bracket portion 36 that is substantially parallel to the plane of the arc formed by the main support member 12 has a plurality of generally parallel grooves 46 formed therein. The grooves 46 may be formed to have a generally V-shaped cross section, which results in a plurality of teeth 48 being formed on the surface 44. The bracket portion 36 preferably includes therein at least two passages 52 and 54, which are preferably threaded to receive a corresponding threaded bolt 56.

Referring to FIG. 1, the end 30 is formed to be substantially similar to the end 28 and includes thereon a bracket portion 58 similar to the bracket portion 36. The bracket portion 58 preferably includes a plurality of grooves 60 and teeth 61 and at least two passages 62 and 64 that are preferably threaded to receive a bolt 66 similar to the bolt 56.

Referring to FIGS. 1 and 3, the coupling assembly 14 includes a bracket portion 68 that may be formed as an elongate thin, rectangular parallelipiped having an elongate passage 70 (FIG. 3) extending between a pair of points 72 and 74 proximate the ends of the longest dimension of the bracket portion 68. The bracket portion 68 includes a plurality of V-shaped grooves 67 between a plurality of teeth 69, which may be interlocked with the grooves 47 and teeth 48 to restrain the bracket portions 36 and 68 against relative movement. The passage 70 has a width that is slightly larger than the diameter of the shaft of the bolt 56 so that the bracket portions 36 and 68 are movable relative to one another while the bolt 56 is engaged in one of the passages 52 or 54, if the grooves 47 and teeth 48 are disengaged from the teeth 69 and the grooves 67, respectively.

Referring to FIG. 3, the bolt 56 has a threaded shaft 73, a head 75 having larger diameter than the shaft 73 and, preferably, a retainer portion 76 between the shaft 73 and the head 75. The head 75 may include a plurality of radial passages 77 therein for receiving a wrench (not shown) to tighten or loosen the engagement between the retaining portion 76 and the surface of the bracket portion 68 around the passage 70. The circumference of the head 74 may be knurled to facilitate manual adjustment thereof. A second bolt 56A may be engaged in one of the passages 52, 54 while the bolt 56 is engaged in the other passage.

As best shown in FIG. 3, the bracket portion 68 extends from a coupler body 80 with the plane in which the grooves 67 are formed being generally perpendicular to a leg 82 of the coupler body 80. The leg 82 is generally rectangular, and the bracket portion 68 is closely adjacent an edge 84 of the leg 82. The bracket portion 68 may be formed integrally with the coupler body 80 or attached thereto by any suitable means, such as welding. When the bracket portions 36 and 68 are assembled together with the slots and teeth engaged, a lower edge 83 of the bracket portion 36 is adjacent the upper surface of the leg 82 at the edge 83. The slots and teeth, the bolt 56 and the proximity of the edge 83 to the leg 82 serve to retain the bracket portions against translational or rotational movement relative to one another.

The coupler body 80 includes a second leg 86 that is substantially perpendicular to the first leg 82. A clamp element 88 formed generally as a cylinder has its curved side 90 connected to the second leg 86 so that the longitudinal axis of the clamp element is generally perpendicular to the second leg 86. The clamp element 88 has a central bore 91 extending therethrough. The central bore 91 is preferably threaded to engage to a bolt 95, shown in FIG. 1, that is substantially identical to the bolt 56. The clamp element 88 may be formed integrally with the second leg 86 or they may be connected by any suitable means, such as welding.

A pair of ears 92 and 94 extend in diametrically opposing relationship from the outer edge of the clamp element 88. The ears 92 and 94 have passages 96 and 98, respectively, therethrough. A cylindrical projection 100 extends outward from the ear 92 around the passage 96. The projection 100 has a plurality of radial slots 104 formed therein. A projection (not shown) similar to the projection 100 extends outward from the ear 94 around the passage 92. The projection 100 may be formed integrally with the ear 92 or the projection 100 may be an elongate sleeve that is welded in or around the passage 96.

The straps 18, 20, 22 and 24 preferably are all substantially identical and are preferably formed as elongate bodies curved in their largest dimension to be approximately arcs of a circle. Each strap, for example the strap 20, includes a plurality of preferably threaded passages 110, shown in FIGS. 1 and 3, for receiving a shaft 112 of a cranial pin 25. A plurality of cranial pins 25 may be mounted in the straps 18, 20 22 and 24 in a generally spherical pattern with the shafts 112 projecting generally radially inward.

Referring to FIG. 3, at an end 114, the strap 20 has a threaded passage 116 therethrough. The passage 116 preferably extends through both the strap 20 and a projection 118 around the passage 116. The projection 118 has a plurality of radial slots 120 and teeth 122 that correspond to the slots 104 and teeth 105 of the projection 100. A bolt 126 similar to the bolt 56 has a shank 128 which passes through the passage 96 and engages the threaded passage 116. When the bolt is tightened to draw the slots 104 and teeth 105 of the ear 92 into registry with the slots 120 and teeth 122 of the strap 20, the strap 20 is rigidly mounted to the coupler body 80 at the ear 92. The bolt 126 may be loosened to disengage the slots 104 and teeth 105 from the slots 120 and teeth 122, and the strap 20 may then be rotated relative to the main support member 12 into a desired position before the bolt 126 is tightened.

The straps 18, 20, 22 and 24 are formed to be substantially identical. The straps 18, 22 and 24 are mounted to their corresponding coupler bodies in a manner similar to that by which the leg 20 is attached to the ear 92 and are similarly rotatable relative to the main support member 12 so when a bolt 128 is loosened from engagement with the ear 94 and the leg 18.

The present invention may be used in conjunction with other orthopedic or traction equipment (not shown). The hanger 34 provides means for applying tension to a patient's spine so that the patient's spine does not have to support the weight of the patient's head and torso. A pair of plates 140, 141 are arranged in parallel relationship and spaced apart by distance slightly larger than the thickness of the main support member 12. A third plate 144 is connected to the two parallel plates by any convenient means, such as welding. The third plate 144 is generally perpendicular to the pair of parallel plates 140, 141 and preferably includes a curved outer edge 146. A plurality of passages 150 are formed in the plate 144 adjacent the curved outer edge 146. The central portion 26 of the main support member 12 includes a plurality of teeth 152 between the notches 32. When the two parallel plates 140, 141 are positioned such that the main support member 12 is in the space between the parallel plates 140,141, a portion 154 of the parallel plates 140, 141 projects beyond the notches 32 and the teeth 152. The projecting portion 154 of the parallel plates 140, 141 has a passage 156 therein, and a pin 160 may be inserted through the passage 156 to engage one of the notches 32 to position the hanger 34 at a desired location on the main support member 12. The pin 160 includes a shank 160A and may include a head 160B having a small orifice 162 therethrough for mounting a wire 164 which extends between the head 160B of the pin 160 and a passage 160 on the plate 144. The wire 164 permits the pin 160 from becoming lost and insures that the wire is always convenient for placing in the passage 156 to lock the hanger 34 to the main support member 12. A double ended hook 170 may be connected into one of the passages adjacent the curved edge of the plate and the other end of the double ended hook may include a keeper 172 to prevent the hook 170 from becoming disconnected from other traction equipment (not shown).

Referring to FIG. 2, the shaft 112 of the Wells Cranial pin 25, with which this particular invention is adapted for use, comprise a hollow cylindrical passage having a hollow head 182. A pin 184 fomred generally in the configuration of a headed nail with a point 186 on one end and a head 188 at the other end is slidably received in the hollow interior of the externally threaded shaft 112. A projection 194 extends from the head 188 toward a passage 196 in the head 182. A compression coil spring 190 rests against the head of the pin and is maintained in the hollow head of the element by a keeper ring 192. When in use, the pin 25 is forced toward and into the skull of the patient by twisting the head 182. The shaft 112, being threadedly received in the pin support means 20, forces the pin 25 towards the patient's skull. Upon application of a predetermined force as determined by the force required to compress the spring 190 until the pin 25 is flush with the opening 196 of the head 182, further turning of the element does not force the pin into the skull of the patient but rather merely causes compression of the spring 190. Other pins (not shown) may be used, but the present invention is conveniently used with the above-described Wells pin.

Ordinarily, when the cervical tong assembly 10 is in use, it is necessary that only one of an opposing pair of pins be one of the Wells Cranial pins described above. For example, referring to FIG. 1, the pins 25 and 25A are in generally opposing; relationship and the pin 25 is shown to be a Wells Cranial pin according to FIG. 2. The pin 25A may have a solid shaft 112A and a solid head 182A without including any of the interior structure shown in FIG. 2. Although in a particular arrangement upon a patient's head, the pins 22 and 25 may not be in perfect opposed alignment, they are sufficiently aligned so that by the well-known action-reaction principal of mechanics, the force exerted by the pin 25A on a patient's skull as determined by the spring will be substantially equal to the force exerted by the pin 25.

All of the cranial pins 25, 25A installed in the cervical tongs assembly 10 have threaded shafts 112 which engage threaded orifices 110 in the corresponding straps 18, 20, 22, and 24. In order to retain the cranial pins 25, 25A at predetermined tensions, a retaiing nut 200 as shown in FIG. 1 may be threadedly attached to the shaft 112 and engaged against the corresponding strap 22, for example.

Referring again to FIG. 1, the coupling assembly 16 includes structure that is substantially identical to that of the coupling assembly 14 and is, therefore, not described in detail.

A clamp element 88A formed to engage the clamp element 88 has a central bore 89 therethrough and is mounted to the clamp element 88 by the bolt 95 extending through the central bore 89 and threadedly engaged with the passage 91 in the clamp element 88. An angled bracket 97 has one leg 97A connected to the clamp element 88A and another leg 97B extending perpendicular from the clamp element 88A generally perpendicular to the leg 97A. The second leg 97B preferably has a passage therethrough for attachment to other cervical traction apparatus, such as a vest (not shown).

The main support 12 cooperates with the hanger 34 to apply to the patient's head a force at a desired angle lying in the plane of the main support member 12. It is not essential to the present invention that the central portion 26 of the main support member 12 includes the notches 32. The entire main support means 12 may be smooth, provided that the hanger 34 includes means for being clamped tighty to any predetermined position on the main support 12. Other means of selectively attaching the hanger to the main support member may also be used; however, the notches and hanger 34, described herein, provide the most convenient, reliable and efficient means presently contemplated for attaching the cervical tongs assembly 10 to other traction apparatus (not shown) for applying a tension to the patient's head at a desired angle.

The brackets provide means for attaching the ends 28 and 30 of the main support 12 to fixation rods (not shown). The use of fixation rods 202 is well-known and is commonly used in connection with the aforementioned halo device (not shown). The lower ends of the fixation rods 202 are commonly secured to a vest (not shown) which fits tightly upon the chest of the patient. The rods 202 extend upwardly from the vest and are secured to the cervical tongs device 10 in a predetermined position with respect to an axis extending upwardly from the center of the patient's head. Ambulatory patients normally use the cervical tongs assembly 10 of the present invention with a vest.

However, when a patient is kept in a fixed position, for example, supine and immobile during initial adjustment of the spine and application of traction, or during traction, the cervical tongs 10 of the present invention may be secured to the fixation rod 202 (not shown) which is in turn secured to a bed or other supporting structure (not shown). Each fixation rod 202 is secured in a relationship so as to apply the force as tension to the head of the user patient at preselected angles measure with reference to a line extending through the center of the patient's head from front to back direction through the head.

The hanger 34, the sliding adjustment permitted by the brackets 36, 68, which provide adjustment of the radial position of the straps 18, 20, 22 and 24 upon the main support 12, and the capability of rotating the straps 18, 20, 22, 24 relative to the main support 12 permits application of a tension vector at any predetermined angle with respect to the head of the patient. Since each of the straps 18, 20, 22 and 24 are independently adjustable, they facilitate attachment to a desire portion of the patient's skull to apply tension at a predetermined angle and to avoid interference with x-rays. The adjustability features of the straps also facilitate placement of the cranial pins 25 in an intact portion of the patient's skull in the case of head injuries and aids in accomodating the cervical tongs 10 to different head sizes.

The cervical traction tongs assembly 10 of the present invention are described with reference to a preferred exemplary embodiment, but the invention is not limited to the specific embodiment described herein. For example, virtually any type of means for attaching the coupling assemblies 14 and 16 to the central support member 12 to adjust the generally radial position of the end of the straps and virtually any means for connecting the straps to the coupling assemblies so that they are independently rotatable relative to the coupling assemblies and to the main support member are regarded as equivalent in structure and function to the essential features of the invention.

Any means that permits the hanger 34 to be connected, clamped or secured selectively along the curved main support member 12 may be regarded as equivalent to the clamp described in the present invention. The main support member 12 is shown and described as a generally curved flat structural element, which is a straightforward and simple configuration for the main support member 12; but any support means which permits the coupling assemblies 14 and 16 to be adjustably attached thereto for movement toward and away from one another will function satisfactorily in the cervical tongs assembly 10. Although the main support member 12 and the straps 18, 20, 22 and 24 are described as being an arc or in an arcuate configuration, there is no criticality to the curvature of the arcs and they need not be circular arcs. Therefore, it is contemplated that those skilled in the art may make modifications in the exemplary preferred embodiment described herein without departing from the spirit and scope of the invention as defined by the appended claims.

What is claimed is:

1. An orthopedic traction tongs assembly for attachment to the head of a user patient by cranial pins for applying tension to the patient's head at selected vector angles measured with reference to a first imaginary axis line extending vertically upward through the center of the patient's head and a second imaginary axis line which orthogonally intersects the first line and extends through the center of the patient's head from front to back, comprising:

main support means formed generally in the configuration of a rigid arc for extending from one side of the patient's head over the top of the patient's head to the other side thereof;

a first coupling assembly connected to a first end of the main support means;

a second coupling assembly connected to the second end of the main support means each coupling assembly being movable on the main support means, generally radially inwardly or outwardly in relation to the arc formed by the main support means;

means for securing each coupling assembly to each end of the main support means, allowing each coupling assembly, to move on the main support means, generally radially inwardly or outwardly in relation to the arc formed by the main support means;

a pair of pin support means connected to each of the first and second coupling assemblies for mounting cranial pins for attachment to the patient's skull, at least one of the pin support means being rotatably mounted to its coupling assembly for permitting attachment of the cranial pin, mounted to the rotatable pin support means, at a selected location on the patient's skull; and a cranial pin, mounted to the rotatable support means, which provides tension at a selected location on patient's skull.

2. The orthopedic traction tongs assembly of claim 1 wherein two pin support means are rotatably mounted to one of the first and second coupling assemblies.

3. The traction tongs assembly of claim 1 wherein each of the first and second coupling assemblies includes:

a first bracket portion on the corresponding end of the main support, said first bracket portion having a plurality of alternating grooves and teeth therein;

a coupler body including a second bracket portion, said second bracket portion including a plurality of grooves and teeth corresponding to the teeth and grooves, respectively, of first bracket portion; and means for selectively securing the first and second bracket portion together with the grooves and teeth thereof secured in interlocking engagement.

4. The orthopedic traction tongs assembly of claim 3 wherein the securing means comprises a threaded passage in the first bracket portion an elongate passage formed in the second bracket portion, and a bolt having a shaft threaded for engagement with the threaded passage and a head for engagement with the second bracket portion when the shaft is inserted through the elongate passage and engaged with the threaded passage.

5. The orthopedic tongs assembly of claim 4 wherein each coupling assembly includes a first leg extending from the coupler body to which the second bracket portion is mounted;

a second leg connected to the first leg and generally perpendicular thereto;

a pair of ears extending from opposite sides of the second leg; and means for securing the pin support means to the ears.

6. The orthopedic traction tongs assembly of claim 5 wherein the means for securing the ears includes:

a passage in each ear;

a plurality of alternating generally radial teeth and grooves formed on each ear around the corresponding passage;

a passage through an end of each pin support means;

a plurality of radial teeth and grooves around the passage in said pin support means; and a bolt for mounting within the passages of the ears and the pin support means for urging the teeth and grooves of the pin support means into locking engagement with the grooves and teeth, respectively of the corresponding ear.

* * * * *